United States Patent
McGovern et al.

(10) Patent No.: US 10,557,832 B2
(45) Date of Patent: Feb. 11, 2020

(54) PORTABLE ACOUSTIC APPARATUS FOR IN-SITU MONITORING OF A WELD IN A WORKPIECE

(71) Applicant: GM GLOBAL TECHNOLOGY OPERATIONS LLC, Detroit, MI (US)

(72) Inventors: Megan E. McGovern, Troy, MI (US); Wayne Cai, Troy, MI (US); Jeffrey A. Abell, Rochester Hills, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 279 days.

(21) Appl. No.: 15/499,957

(22) Filed: Apr. 28, 2017

(65) Prior Publication Data

US 2018/0313790 A1 Nov. 1, 2018

(51) Int. Cl.
| | |
|---|---|
| *G01N 29/24* | (2006.01) |
| *G01N 29/28* | (2006.01) |
| *G01N 29/26* | (2006.01) |
| *G01N 29/265* | (2006.01) |
| *G01N 29/06* | (2006.01) |

(Continued)

(52) U.S. Cl.
CPC ........ *G01N 29/2437* (2013.01); *G01N 29/043* (2013.01); *G01N 29/0654* (2013.01); *G01N 29/221* (2013.01); *G01N 29/262* (2013.01); *G01N 29/265* (2013.01); *G01N 29/28* (2013.01); *G01N 2291/0234* (2013.01); *G01N 2291/0235* (2013.01); *G01N 2291/048* (2013.01); *G01N 2291/102* (2013.01); *G01N 2291/106* (2013.01); *G01N 2291/267* (2013.01); *G01N 2291/2638* (2013.01); *G01N 2291/2677* (2013.01)

(58) Field of Classification Search
CPC ..... G01N 2291/267; G01N 2291/2677; G01N 2291/048; G01N 2291/106; G01N 2291/2638
See application file for complete search history.

(56) References Cited

U.S. PATENT DOCUMENTS

| | | | | |
|---|---|---|---|---|
| 3,726,130 | A | * 4/1973 | Hurlebaus | G01N 29/043 73/629 |
| 5,267,221 | A | * 11/1993 | Miller | G10K 11/002 310/327 |

(Continued)

*Primary Examiner* — Natalie Huls
(74) *Attorney, Agent, or Firm* — Quinn IP Law

(57) ABSTRACT

An apparatus for in-situ monitoring of a welded joint in a workpiece includes an ultrasonic sending transducer and a receiving transducer. The ultrasonic sending transducer includes a probe head disposed on a plurality of individually-activatable piezoelectric elements, and a plurality of waveguide probes projecting orthogonally from a planar surface. A wave attenuator is disposed between individual ones of the waveguide probes. A receiving transducer is disposed therein. The workpiece is insertable between the waveguide probes of the ultrasonic sending transducer and the receiving transducer. The ultrasonic sending transducer urges the probe head towards the receiving transducer such that the waveguide probes physically contact the welded joint in the workpiece. The piezoelectric elements individually excite the waveguide probe that is in physical contact with the welded joint in the workpiece. The acoustic receiving transducer is disposed to monitor the welded joint in the workpiece.

12 Claims, 3 Drawing Sheets

(51) Int. Cl.
*G01N 29/22* (2006.01)
*G01N 29/04* (2006.01)

(56) References Cited

U.S. PATENT DOCUMENTS

| | | | | |
|---|---|---|---|---|
| 5,533,401 A * | 7/1996 | Gilmore | ............ | G01N 29/0609 73/620 |
| 5,644,085 A * | 7/1997 | Lorraine | ............ | B06B 1/0629 29/25.35 |
| 5,677,490 A * | 10/1997 | Gunther | ............ | G01N 29/043 73/620 |
| 5,728,937 A * | 3/1998 | Reichau | ............ | G01M 7/022 73/579 |
| 5,777,229 A * | 7/1998 | Geier | ............ | G01N 29/2412 228/104 |
| 5,920,014 A * | 7/1999 | Waschkies | ............ | B23K 11/252 73/597 |
| 6,116,090 A * | 9/2000 | Maev | ............ | G10K 11/35 73/618 |
| 6,546,803 B1 * | 4/2003 | Ptchelintsev | ............ | B06B 1/0622 73/625 |
| 7,036,376 B2 * | 5/2006 | Arndt | ............ | B23K 11/257 219/109 |
| 8,183,493 B2 * | 5/2012 | Batzinger | ............ | B23K 11/252 219/109 |
| 2002/0172620 A1 * | 11/2002 | Potyrailo | ............ | G01N 29/02 422/82.02 |
| 2003/0154031 A1 * | 8/2003 | Potyrailo | ............ | G01N 29/022 702/19 |
| 2004/0249589 A1 * | 12/2004 | Coperet | ............ | G01N 29/0645 702/79 |
| 2006/0076321 A1 * | 4/2006 | Maev | ............ | B23K 11/252 219/109 |
| 2006/0260403 A1 * | 11/2006 | Waschkies | ............ | B23K 9/095 73/588 |
| 2007/0282543 A1 * | 12/2007 | Hiyama | ............ | G01N 29/06 702/39 |
| 2009/0283569 A1 * | 11/2009 | Ramaswamy | ............ | B23K 11/252 228/1.1 |
| 2013/0255384 A1 * | 10/2013 | Putsherry | ............ | G01N 29/262 73/588 |
| 2015/0272544 A1 * | 10/2015 | Raum | ............ | A61B 8/429 600/438 |
| 2015/0308982 A1 * | 10/2015 | Perrin | ............ | G01N 29/043 73/588 |
| 2015/0308984 A1 * | 10/2015 | Coulette | ............ | G01N 29/265 73/588 |
| 2015/0369779 A1 * | 12/2015 | Kawamoto | ............ | B23K 20/10 73/588 |
| 2016/0169840 A1 * | 6/2016 | Todorov | ............ | G01N 29/0645 73/588 |
| 2016/0231291 A1 * | 8/2016 | Boulware | ............ | G01N 29/262 |
| 2016/0320344 A1 * | 11/2016 | Spencer | ............ | G01N 29/043 |
| 2017/0276651 A1 * | 9/2017 | Hall | ............ | G01B 17/02 |
| 2017/0284971 A1 * | 10/2017 | Hall | ............ | G01B 17/02 |
| 2018/0106765 A1 * | 4/2018 | Kim | ............ | G01N 29/069 |
| 2018/0113100 A1 * | 4/2018 | St-Laurent | ............ | G01B 17/06 |
| 2018/0143164 A1 * | 5/2018 | Rousseau | ............ | G01N 29/069 |
| 2018/0238834 A1 * | 8/2018 | Sekiguchi | ............ | G01N 29/041 |
| 2018/0364199 A1 * | 12/2018 | Pahlavan | ............ | G01N 29/043 |

* cited by examiner

US 10,557,832 B2

PORTABLE ACOUSTIC APPARATUS FOR IN-SITU MONITORING OF A WELD IN A WORKPIECE

INTRODUCTION

Evaluation devices and methods may employ ultrasonic or other acoustic signals.

SUMMARY

An apparatus for in-situ monitoring of a welded joint in a workpiece is described, and includes an ultrasonic sending transducer and a receiving transducer. The ultrasonic sending transducer includes a probe head disposed on a plurality of individually-activatable piezoelectric elements. The probe head includes a plurality of waveguide probes projecting orthogonally from a planar surface thereof. A wave attenuator is disposed between individual ones of the waveguide probes. A receiving transducer is disposed therein. The workpiece is insertable between the waveguide probes of the ultrasonic sending transducer and the receiving transducer. The ultrasonic sending transducer is disposed to urge the probe head towards the receiving transducer such that at least one of the waveguide probes physically contacts the welded joint in the workpiece. The piezoelectric elements are controllable to individually excite the at least one waveguide probe that is in physical contact with the welded joint in the workpiece. The acoustic receiving transducer is disposed to monitor the welded joint in the workpiece.

An aspect of the disclosure includes the ultrasonic sending transducer being disposed to urge the probe head towards the receiving transducer such that at least one of the waveguide probes is in physical contact with a bonding area of the welded joint in the workpiece.

Another aspect of the disclosure includes a controller in communication with the individually-activatable piezoelectric elements of the ultrasonic sending transducer and the acoustic receiving transducer, wherein the controller is disposed to command operation of at least one of the individually-activatable piezoelectric elements that is associated with one of the waveguide probes of the ultrasonic sending transducer, and the controller is disposed to monitor the acoustic receiving transducer.

Another aspect of the disclosure includes the plurality of individually-activatable piezoelectric elements being disposed in a rectilinear grid array, wherein each of the piezoelectric elements is associated with only one of the waveguide probes.

Another aspect of the disclosure includes each of the waveguide probes including a tip portion that is configured to be conformable to a bonding area of the welded joint in the workpiece, wherein a dry couplant is attached to the tip portion.

Another aspect of the disclosure includes the dry couplant attached to the tip portion being a polymer.

Another aspect of the disclosure includes the weld joint of the workpiece including a plurality of weld troughs arranged in a pre-defined topography, wherein the plurality of waveguide probes are disposed on the probe head in correspondence to the plurality of weld troughs of the pre-defined topography.

Another aspect of the disclosure includes the acoustic receiving transducer being an acoustography film.

Another aspect of the disclosure includes the acoustic receiving transducer being a multi-element acoustic receiving transducer arranged in a rectilinear array.

Another aspect of the disclosure includes the acoustic receiving transducer being a flat surface.

Another aspect of the disclosure includes the probe head being disposed on the ultrasonic sending transducer including a first configuration of waveguide probes projecting orthogonally from the surface thereof, and the probe head being replaceable with a second probe head having a second configuration of the waveguide probes projecting orthogonally from the surface thereof, wherein the first configuration of waveguide probes has an arrangement that differs from the second configuration of waveguide probes.

Another aspect of the disclosure includes the first configuration of waveguide probes including a plurality of waveguide probes, and the second configuration of waveguide probes including a single waveguide probe.

Another aspect of the disclosure includes the apparatus for in-situ monitoring of a welded joint in a workpiece being operable to provide in-situ non-destructive testing and examination of a welded joint in a workpiece absent immersion in a fluidic bath or application of a gel/fluid couplant.

The above features and advantages, and other features and advantages, of the present teachings are readily apparent from the following detailed description of some of the best modes and other embodiments for carrying out the present teachings, as defined in the appended claims, when taken in connection with the accompanying drawings.

BRIEF DESCRIPTION OF THE DRAWINGS

One or more embodiments will now be described, by way of example, with reference to the accompanying drawings, in which.

DETAILED DESCRIPTION

Figure 1:
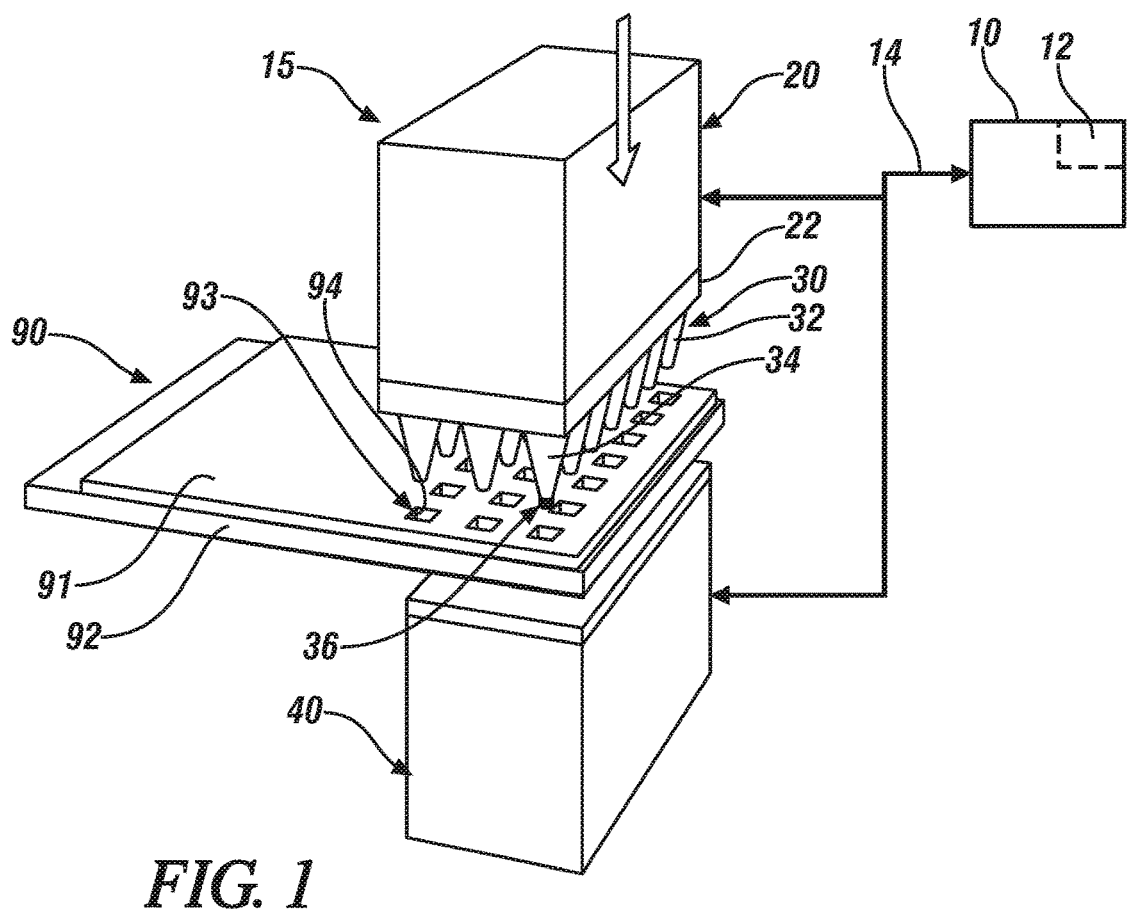
FIG. 1 schematically shows an isometric drawing of an apparatus including an ultrasonic sending transducer and a receiving transducer for in-situ monitoring of a welded joint in a workpiece, in accordance with the disclosure.

The components of the disclosed embodiments, as described and illustrated herein, may be arranged and designed in a variety of different configurations. Thus, the following detailed description is not intended to limit the scope of the disclosure, as claimed, but is merely representative of possible embodiments thereof. In addition, while numerous specific details are set forth in the following description in order to provide a thorough understanding of the embodiments disclosed herein, some embodiments can be practiced without some of these details. Moreover, for the purpose of clarity, certain technical material that is known in the related art has not been described in detail in order to avoid unnecessarily obscuring the disclosure. Furthermore, the drawings are in simplified form and are not to precise scale. For purposes of convenience and clarity only, directional terms such as top, bottom, left, right, up, over, above, below, beneath, rear, and front, may be used with respect to the drawings. These and similar directional terms are not to be construed to limit the scope of the disclosure. Furthermore, the disclosure as illustrated and described herein may be practiced in the absence of an element that is not specifically disclosed herein.

Referring now to the drawings, which are provided for the purpose of illustrating certain exemplary embodiments only and not for the purpose of limiting the same, FIGS. 1, 2, 3, 4 and 5 schematically illustrate various elements, perspectives and details of a monitoring apparatus 15 that is configured to provide in-situ non-destructive testing and examination of a welded joint 93 in a workpiece 90, wherein the monitoring apparatus includes an ultrasonic sending transducer 20 and an acoustic receiving transducer 40 that are operated by a controller 10. Like numerals indicate like elements in the various illustrations. The welded joint 93 of the workpiece 90 is shown as a lap joint that is effected by ultrasonic welding, but the concepts described herein may be applied to other welded joints that are achieved by other welding processes, such as spot welds or bonding. In one embodiment and as shown, the welded joint 93 of the workpiece 90 is interposed between the ultrasonic sending transducer 20 and the acoustic receiving transducer 40 to effect the in-situ monitoring of the welded joint 93. This can be accomplished by moving the workpiece 90 into a suitable position between the ultrasonic sending transducer 20 and the acoustic receiving transducer 40, or by moving the ultrasonic sending transducer 20 and the acoustic receiving transducer 40 into a suitable position around the workpiece 90, depending upon the specific configuration. The monitoring apparatus 15 including the ultrasonic sending transducer 20 and the acoustic receiving transducer 40 can be advantageously deployed in a manufacturing setting for in-line weld quality inspection in a production line. The monitoring apparatus 15 including the ultrasonic sending transducer 20 and the acoustic receiving transducer 40 is operable to provide in-situ non-destructive testing and examination of a welded joint 93 in a workpiece 90 absent immersion of the apparatus in a fluidic bath or application of a gel/fluid couplant.

In one embodiment and as shown the welded lap joint 93 of the workpiece 90 is formed between a first element 91 and a second element 92, wherein the first element 91 is lapped with the second element 92 and welded together employing a vibrational welding tool. The first element 91 and the second element 92 may be fabricated from suitable composite polymer materials or metal alloys. The process of vibrational welding can generate the welded joint 93 that includes one or a plurality of bonding areas in the form of weld troughs 94 that are caused by a combination of compressive load and vibration that are applied by a sonotrode tip (not shown) to the workpiece 90 during vibrational welding. Other welding processes can result in other forms of bonding areas associated with a welded joint, which can be subjected to in-situ non-destructive testing and examination employing an embodiment of the monitoring apparatus 15 described herein.

The ultrasonic sending transducer 20 includes a probe head 30 that is disposed on a plurality of individually-activatable piezoelectric elements 22. The probe head 30 can include a single waveguide probe (shown as element 632 in FIG. 6) or a plurality of waveguide probes 32 that project orthogonally from a planar surface of the probe head 30. The probe head 30 is preferably fabricated as a unitary device having a base portion and a plurality of waveguide probes 32, as shown. The probe head 30 can be fabricated using three-dimensional printing, machining or another suitable fabrication method and process. The ultrasonic sending transducer 20 is preferably configured so that the probe head 30 is replaceable and interchangeable with various probe head configurations, such as the probe head 630 that is shown with reference to FIG. 6. Details of the configuration and design for a probe head are selected based upon the specific geometry and arrangement of the welded joint of the workpiece, such as the illustrated probe head 30 having waveguide probes 32 that correspond to the weld troughs 94 of the welded joint 93 of the workpiece 90 shown with reference to FIG. 1. In one embodiment, the welded joint 93 of the workpiece 90 includes a plurality of weld troughs 94 that are arranged in a pre-defined topography, e.g., a rectilinear arrangement, and the waveguide probes 32 are arranged on the probe head 30 to conform to the pre-defined topography of the plurality of weld troughs 94.

Each of the waveguide probes 32 includes a tip portion 34 that is configured to be conformable to the weld trough 94 of the welded joint 93 in the workpiece 90, and a dry couplant 36 can be attached to the tip portion 34 such that the dry couplant 36 is interposed between the tip portion of the waveguide probe 32 and the weld trough 94 of the welded joint 93 during operation. Examples of a dry couplant 36 include a silicone insert, plastic sheeting, cellophane, a rubberize insert, a polymeric insert, etc. The dry couplant 36 is employed to facilitate vibrational coupling between the waveguide probe 32 and the weld trough 94. This arrangement eliminates any need for immersing the workpiece 90 into a liquid to effect the measurement.

A wave attenuator 38 (shown with reference to FIG. 5) can be interposed between the individual waveguide probes 32 of the probe head 30. The wave attenuator 38 includes, in one embodiment, a plurality of interlocked elements having corrugated surfaces that are arranged in a rectilinear fashion and interposed between individual ones of the waveguide probes 32. The wave attenuator 38 absorbs vibration energy that may propagate from an activated one of the waveguide probes 32 across the probe head 30. The wave attenuator 38 vibrationally decouples the individual waveguide probes 32 when the probe head 30 with a plurality of waveguide probes 32 is fabricated as a unitary device. The vibrational decoupling of the wave attenuator 38 avoids or minimizes unintended wave modes and cross-talk between adjacent waveguides 32 on the probe head 30 during operation of the monitoring apparatus 15.

Figure 2:
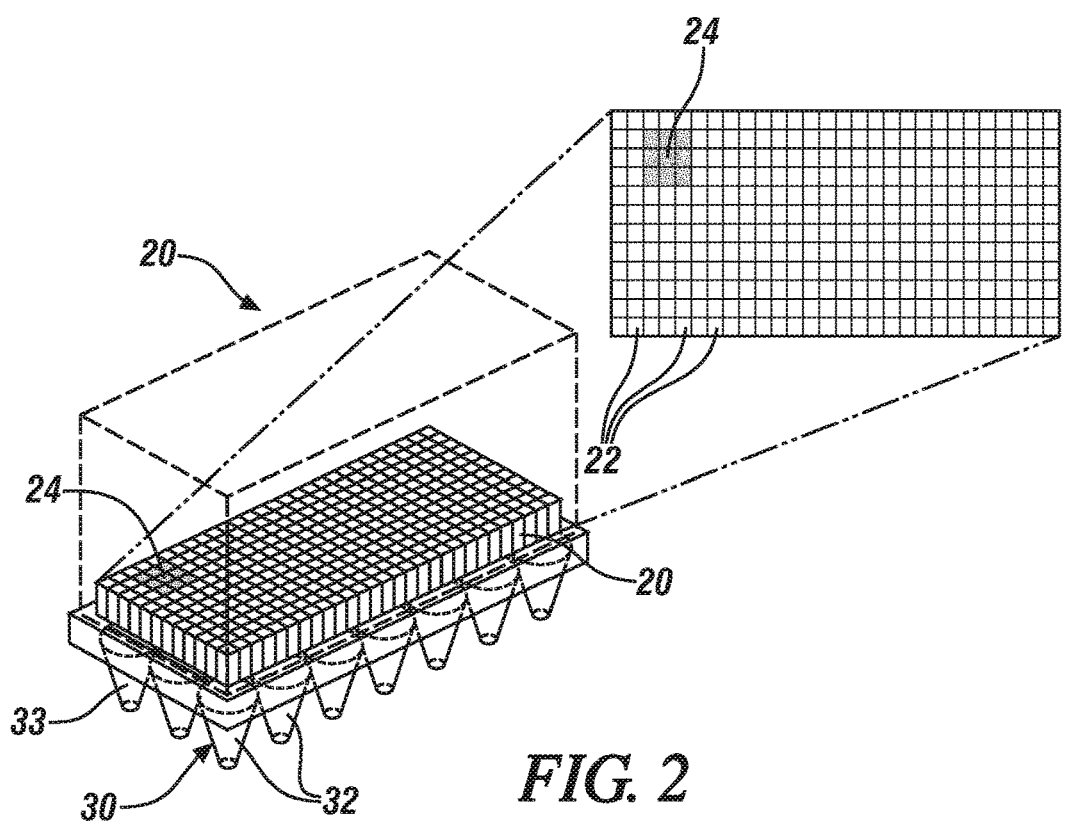
FIG. 2 schematically shows an isometric drawing of an apparatus for in-situ monitoring of a welded joint in a workpiece that includes details related to arrangement and selective activation of piezoelectric elements disposed in the ultrasonic sending transducer, in accordance with the disclosure.
Figure 3:
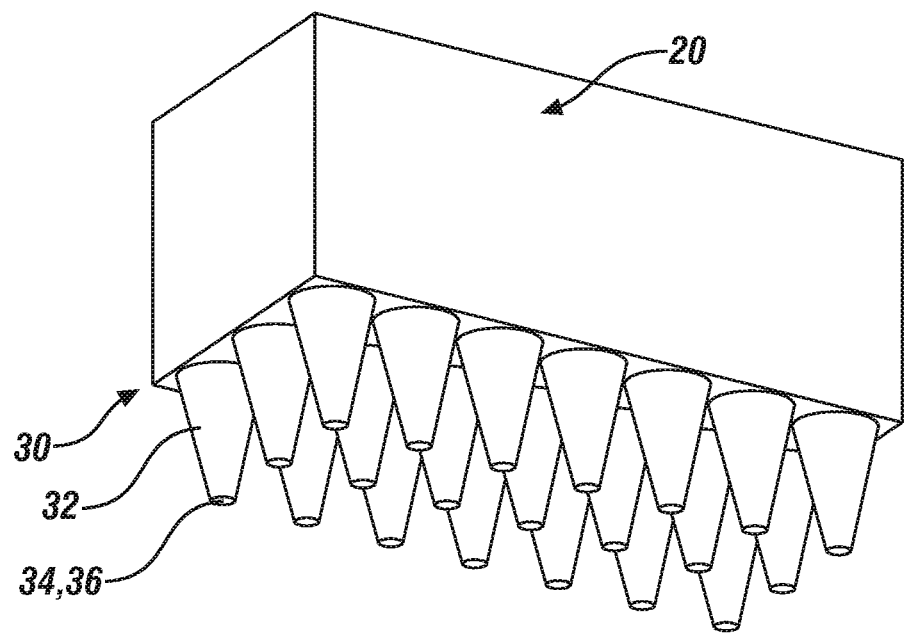
FIG. 3 schematically shows an isometric drawing of an apparatus for in-situ monitoring of a welded joint in a workpiece that includes details related to a probe head having a plurality of waveguide probes for the ultrasonic sending transducer, in accordance with the disclosure.
Figure 4:
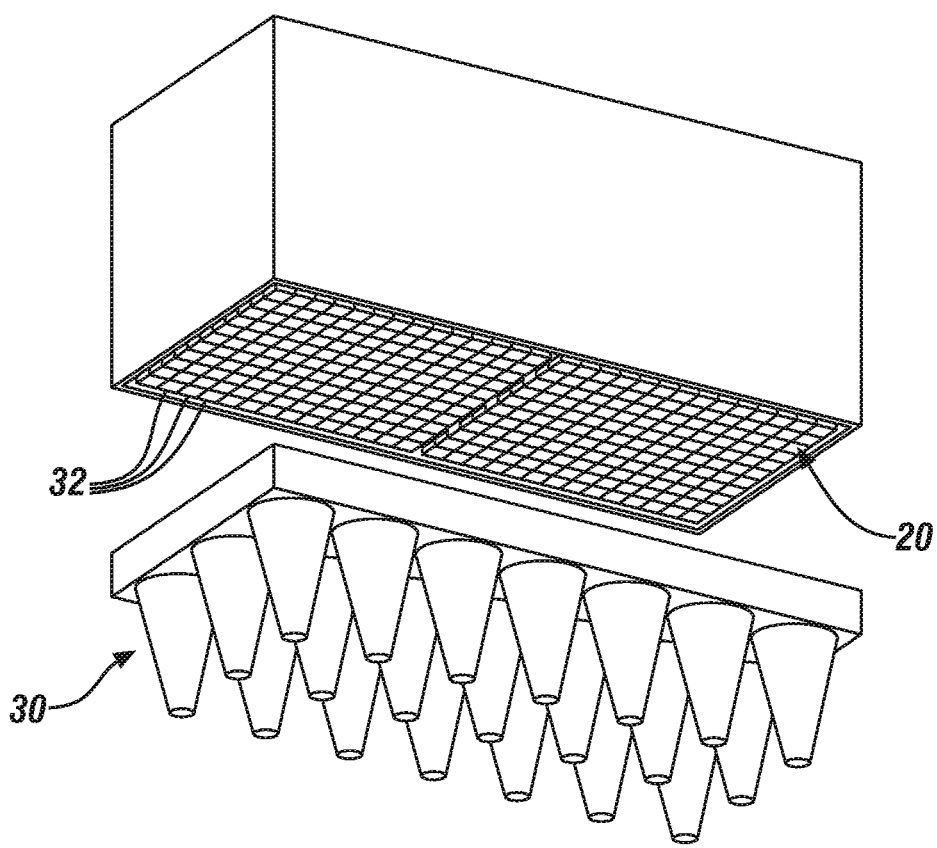
FIG. 4 schematically shows an exploded isometric drawing of an apparatus for in-situ monitoring of a welded joint in a workpiece that includes details related to a probe head and waveguide probes for the ultrasonic sending transducer, in accordance with the disclosure.
Figure 5:
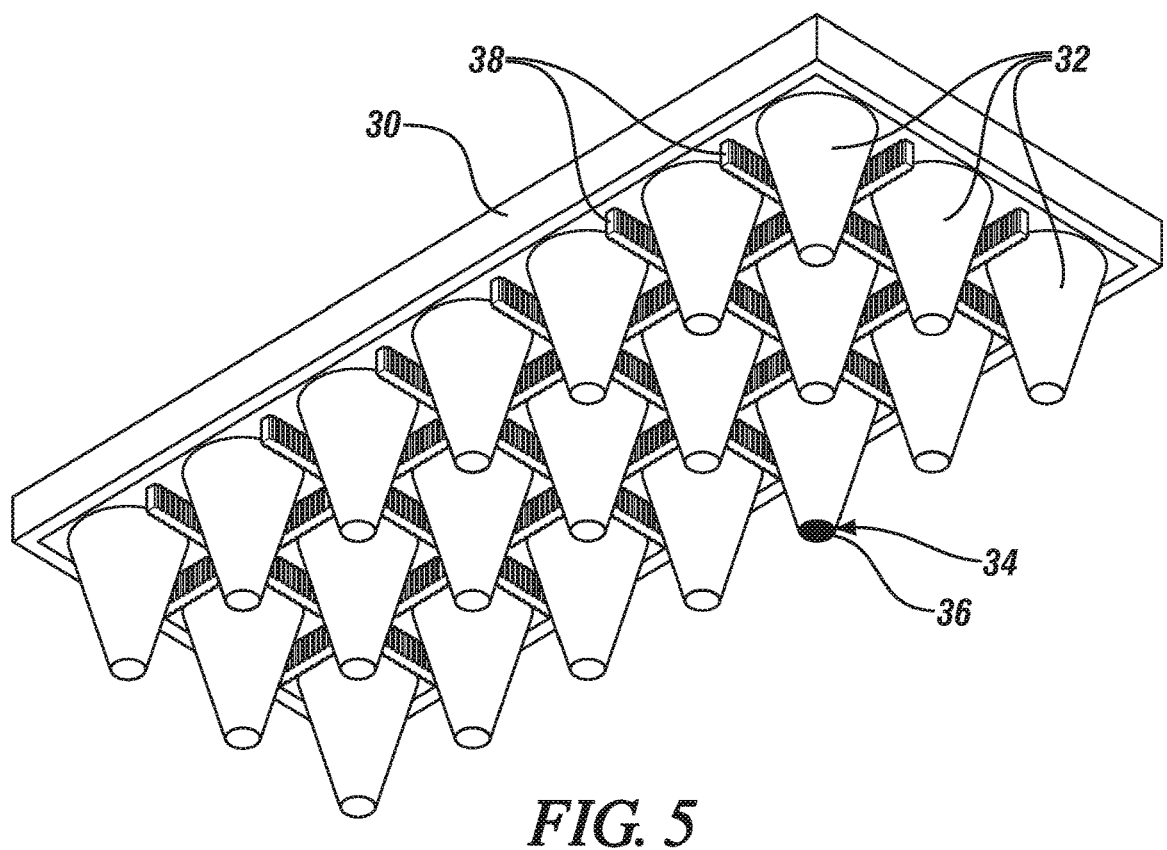
FIG. 5 schematically shows an isometric drawing of an apparatus for in-situ monitoring of a welded joint in a workpiece that includes details related to a probe head having a plurality of waveguide probes and a wave attenuator for the ultrasonic sending transducer, in accordance with the disclosure.

The plurality of individually-activatable piezoelectric elements 22 are preferably arranged in a rectilinear grid, e.g., as shown with reference to FIG. 2. Each of the piezoelectric elements 22 is in communication with the controller 10 via communication link 14. The controller 10 includes a control routine 12 that is executable to command and control individual activation and deactivation of each of the piezoelectric elements 22. By way of a non-limiting example, the view of the piezoelectric elements 22 that is shown with reference to FIG. 2 includes nine of the piezoelectric elements, which are shaded and identified by numeral 24, indicating that they are selectively activatable, as described hereinbelow.

Continuing to refer to FIG. 2, the nine selectively activated piezoelectric elements 24 are physically adjacent to and in vibrational communication with one of the waveguide probes, which is indicated by numeral 33. In operation, vibration energy that is generated by activation of the piezoelectric elements 24 is transmitted only to the waveguide probe 33 of the probe head 30. No vibration energy is directly transmitted to the other waveguide probes 32 of the probe head 30 via the non-activated piezoelectric elements 22. As such, the piezoelectric elements 22 that are activated are those that align with an appropriate feature of the specific embodiment of the probe head 30, for example, only the piezoelectric elements 24 that are positioned over the selected waveguide probe 33 will be activated in one case. As such, the piezoelectric elements 22 can be controlled to individually excite one or a plurality of waveguide probes 32 that is in physical contact with a weld trough 94 that is a portion of the welded joint 93 in the workpiece 90. Some of the piezoelectric elements 22 may not be associated with any of the waveguide probes 32. For example, there can be unused elements. Furthermore, more than one of the piezoelectric elements 22 can be assigned to and in vibrational communication with the same one of the waveguide probes 32.

The ultrasonic sending transducer 20 can be disposed in a device (not shown) that includes one or a plurality of elements that exert a compressive load 21 to urge the probe head 30 towards the acoustic receiving transducer 40 such that at least one of the waveguide probes 32 physically contacts and preferably applies a compressive load onto the welded joint 93 in the workpiece 90.

The acoustic receiving transducer 40 can be an acoustography sensing system that includes acoustography film, camera, light source, etc. in one embodiment. The acoustography sensing system includes a film that reacts to ultrasound, thus enabling capture of acoustic scan signals without scanning. Alternatively, the acoustic receiving transducer 40 may be a scanning type application, such as a rectilinear array that is subjected to a phased array scan, an amplitude/time scan, or a paint brush-type scan device. Preferably the acoustic receiving transducer 40 is disposed as a flat surface.

The controller 10 is in communication with the individually-activatable piezoelectric elements 22 of the ultrasonic sending transducer 20 and with the acoustic receiving transducer 40. In operation, the controller 10 can command operation of the ultrasonic sending transducer 20 to apply compressive force 21 to a sample workpiece 90. This permits each of the waveguide probes 32 to have intimate contact with one of the weld troughs 94 of the welded joint 93, affording a precise measurement that is focused only on the area of interest, i.e., the weld trough 94.

The controller 10 can command operation of at least one of the individually-activatable piezoelectric elements 22 that is associated with one of the waveguide probes 32 of the ultrasonic sending transducer 20, with such operation being in the form of a voltage or force amplitude-time scan (A scan). The controller 10 further monitors signal outputs from the acoustic receiving transducer 40, which are subject to signal processing to evaluate one or a plurality of the weld troughs 94 of the welded joint 93. This operation can execute to step through and sequentially activate the piezoelectric elements 22 and monitor the output with the acoustic receiving transducer 40, in one embodiment. Alternatively, this operation can execute to step through and sequentially activate subsets of the piezoelectric elements 22 and monitor the output with the acoustic receiving transducer 40. Alternatively, this operation can execute to simultaneously activate the piezoelectric elements 22 and monitor the output with the acoustic receiving transducer 40. Such operations can be reduced to algorithmic code that is executed as the control routine 12 that preferably stored in an executable in the controller 10.

Figure 6:
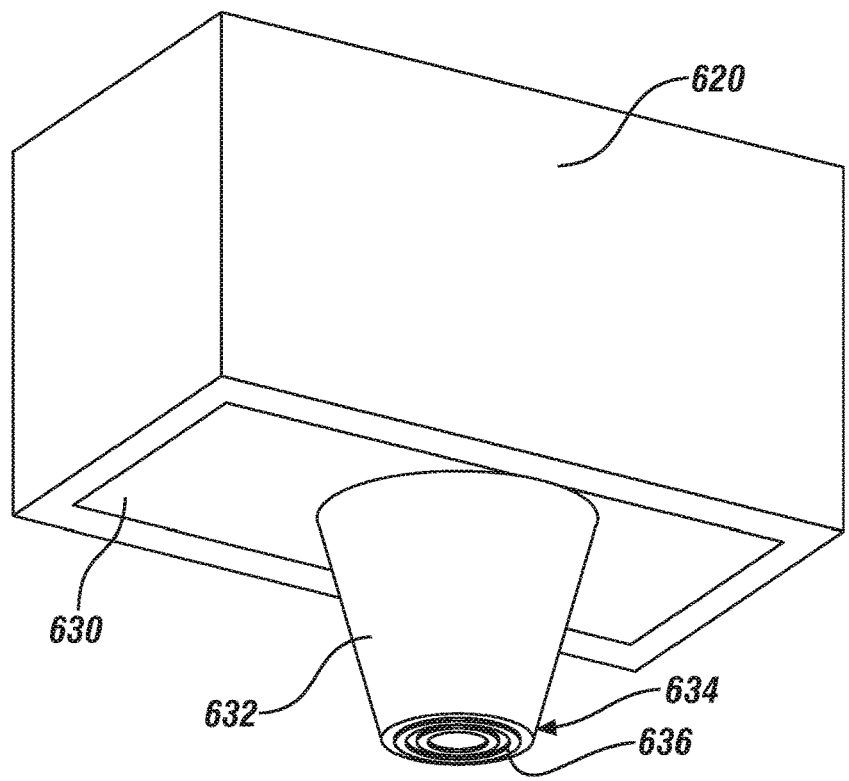
FIG. 6 schematically shows an isometric drawing of an apparatus for in-situ monitoring of a welded joint in a workpiece that includes details related to another embodiment of a probe head having a single waveguide probe for the ultrasonic sending transducer, in accordance with the disclosure.

FIG. 6 illustrates an ultrasonic sending transducer 620 including a probe head 630 having a single waveguide probe 632 that includes a tip portion 634 with a dry couplant 636 attached thereto, which may be designed and employed to monitor a spot weld, a bead weld, a rivet, an ultrasonic weld, or another bonding geometry. As such, the probe head is customizable and reconfigurable.

The term "controller" and related terms such as control module, module, control, control unit, processor and similar terms refer to one or various combinations of Application Specific Integrated Circuit(s) (ASIC), electronic circuit(s), central processing unit(s), e.g., microprocessor(s) and associated non-transitory memory component(s) in the form of memory and storage devices (read only, programmable read only, random access, hard drive, etc.). The non-transitory memory component is capable of storing machine readable instructions in the form of one or more software or firmware programs or routines, combinational logic circuit(s), input/output circuit(s) and devices, signal conditioning and buffer circuitry and other components that can be accessed by one or more processors to provide a described functionality. Input/output circuit(s) and devices include analog/digital converters and related devices that monitor inputs from sensors, with such inputs monitored at a preset sampling frequency or in response to a triggering event. Software, firmware, programs, instructions, control routines, code, algorithms and similar terms mean controller-executable instruction sets including calibrations and look-up tables. Each controller executes control routine(s) to provide desired functions. Routines may be executed at regular intervals, for example each 100 microseconds during ongoing operation. Alternatively, routines may be executed in response to occurrence of a triggering event. Communication between controllers, and communication between controllers, actuators and/or sensors may be accomplished using a direct wired point-to-point link, a networked communication bus link, a wireless link or another suitable communication link, and is indicated by line 14. Communication includes exchanging data signals in suitable form, including, for example, electrical signals via a conductive medium, electromagnetic signals via air, optical signals via optical waveguides, and the like. The data signals may include discrete, analog or digitized analog signals representing inputs from sensors, actuator commands, and communication between controllers. The term "signal" refers to a physically discernible indicator that conveys information, and may be a suitable waveform (e.g., electrical, optical, magnetic, mechanical or electromagnetic), such as DC, AC, sinusoidal-wave, triangular-wave, square-wave, vibration, and the like, that is capable of traveling through a medium.

The detailed description and the drawings or figures are supportive and descriptive of the present teachings, but the scope of the present teachings is defined solely by the claims. While some of the best modes and other embodiments for carrying out the present teachings have been described in detail, various alternative designs and embodiments exist for practicing the present teachings defined in the appended claims.

What is claimed is:

1. An apparatus for in-situ monitoring of a welded joint in a workpiece, comprising:
   an ultrasonic sending transducer and a receiving transducer;
   the ultrasonic sending transducer including a probe head disposed on a plurality of individually-activatable piezoelectric elements;
   the probe head including a plurality of waveguide probes projecting orthogonally from a planar surface thereof, wherein each of the waveguide probes includes a tip portion that is configured to be conformable to a bonding area of the welded joint in the workpiece, and wherein a dry couplant is attached to the tip portion;
   a wave attenuator disposed between individual ones of the waveguide probes; and
   a receiving transducer;
   wherein the workpiece is insertable between the waveguide probes of the ultrasonic sending transducer and the receiving transducer;
   wherein the ultrasonic sending transducer is disposed to urge the probe head towards the receiving transducer such that at least one of the waveguide probes physically contacts the welded joint in the workpiece;
   wherein the piezoelectric elements are controllable to individually excite the at least one waveguide probe that is in physical contact with the welded joint in the workpiece; and
   wherein the acoustic receiving transducer is disposed to monitor the welded joint in the workpiece.

2. The apparatus of claim 1, wherein the ultrasonic sending transducer is disposed to urge the probe head towards the receiving transducer such that at least one of the waveguide probes is in physical contact with a bonding area of the welded joint in the workpiece.

3. The apparatus of claim 1, further comprising:
   a controller in communication with the individually-activatable piezoelectric elements of the ultrasonic sending transducer and the acoustic receiving transducer;
   wherein the controller is disposed to command operation of at least one of the individually-activatable piezoelectric elements that is associated with one of the waveguide probes of the ultrasonic sending transducer; and
   wherein the controller is disposed to monitor the acoustic receiving transducer.

4. The apparatus of claim 1, wherein the plurality of individually-activatable piezoelectric elements are disposed in a rectilinear grid array, and wherein each of the piezoelectric elements is associated with only one of the waveguide probes.

5. The apparatus of claim 1, wherein the dry couplant attached to the tip portion comprises a polymeric insert.

6. The apparatus of claim 1, wherein the welded joint of the workpiece includes a plurality of weld troughs arranged in a pre-defined topography; and wherein the plurality of waveguide probes are disposed on the probe head in correspondence to the arrangement of the plurality of weld troughs of the pre-defined topography.

7. The apparatus of claim 1, wherein the acoustic receiving transducer comprises an acoustography film.

8. The apparatus of claim 1, wherein the acoustic receiving transducer comprises a multi-element acoustic receiving transducer arranged in a rectilinear array.

9. The apparatus of claim 1, wherein the acoustic receiving transducer comprises a flat surface.

10. An apparatus for in-situ monitoring of a welded joint in a workpiece, comprising:
    an ultrasonic sending transducer and a receiving transducer;
    the ultrasonic sending transducer including a probe head disposed on a plurality of individually-activatable piezoelectric elements;
    the probe head including a plurality of waveguide probes projecting orthogonally from a planar surface thereof, wherein the probe head includes a first configuration of waveguide probes projecting orthogonally from the surface thereof; and wherein the probe head is replaceable with a second probe head having a second configuration of the waveguide probes projecting orthogonally from the surface thereof, wherein the first configuration of waveguide probes has an arrangement that differs from the second configuration of waveguide probes;
    a wave attenuator disposed between individual ones of the waveguide probes; and
    a receiving transducer;
    wherein the workpiece is insertable between the waveguide probes of the ultrasonic sending transducer and the receiving transducer;
    wherein the ultrasonic sending transducer is disposed to urge the probe head towards the receiving transducer such that at least one of the waveguide probes physically contacts the welded joint in the workpiece;
    wherein the piezoelectric elements are controllable to individually excite the at least one waveguide probe that is in physical contact with the welded joint in the workpiece; and
    wherein the acoustic receiving transducer is disposed to monitor the welded joint in the workpiece.

11. The apparatus of claim 10, wherein the first configuration of waveguide probes includes a plurality of waveguide probes and wherein the second configuration of waveguide probes includes a single waveguide probe.

12. The apparatus of claim 10, wherein the apparatus for in-situ monitoring of a welded joint in a workpiece is operable absent immersion of the workpiece into a fluidic bath or application of a gel/fluid couplant.

* * * * *